US00PP21703P2

(12) United States Plant Patent
Lemon

(10) Patent No.: US PP21,703 P2
(45) Date of Patent: Feb. 8, 2011

(54) ***GERANIUM* PLANT NAMED 'OGLGER579'**

(50) Latin Name: *Pelargonium×domesticum*
Varietal Denomination: Oglger579

(75) Inventor: David G. Lemon, Lompoc, CA (US)

(73) Assignee: Ecke Geraniums, LLC, Encinitas, CA (US)

( * ) Notice: Subject to any disclaimer, the term of this patent is extended or adjusted under 35 U.S.C. 154(b) by 7 days.

(21) Appl. No.: 12/462,088

(22) Filed: Jul. 29, 2009

(51) Int. Cl.
*A01H 5/00* (2006.01)

(52) U.S. Cl. ..... Plt./331
(58) Field of Classification Search ..... Plt./331
See application file for complete search history.

(56) References Cited

U.S. PATENT DOCUMENTS

PP10,000 P * 8/1997 Lemon ..... Plt./331
PP13,522 P3 * 1/2003 Lemon ..... Plt./331

OTHER PUBLICATIONS

UPOV ROM GTITM Computer Database, GTI Jouve Retrival Software 2010/03 Citation for 'Oglger579'.*

* cited by examiner

*Primary Examiner*—Wendy C. Haas
(74) *Attorney, Agent, or Firm*—C. A. Whealy

(57) ABSTRACT

A new and distinct cultivar of Regal *Geranium* plant named 'Oglger579', characterized by its upright to outwardly spreading and mounded plant habit; freely branching habit; freely flowering habit; and large pink and red purple bi-colored flowers.

1 Drawing Sheet

Botanical designation: *Pelargonium×domesticum.*
Cultivar denomination: 'OGLGER579'.

BACKGROUND OF THE INVENTION

The present invention relates to a new and distinct cultivar of Regal *Geranium* plant, botanically known as *Pelargonium×domesticum*, and hereinafter referred to by the name 'Oglger579'.

The new Regal *Geranium* plant is a product of a planned breeding program conducted by the Inventor in Lompoc, Calif. The objective of the breeding program is to create new medium-sized and early and freely flowering Regal *Geranium* cultivars with large and attractive flowers.

The new Regal *Geranium* plant originated from a cross-pollination made by the Inventor in March, 1998 in Lompoc, Calif. of a proprietary selection of *Pelargonium×domesticum* identified as code number 269, not patented, as the female, or seed, parent with a proprietary selection of *Pelargonium×domesticum* identified as code number 101, not patented, as the male, or pollen, parent. The new Regal *Geranium* was discovered and selected by the Inventor as a single flowering plant from within the progeny of the stated cross-pollination in a controlled greenhouse environment in Connellsville, Pa. in February, 2000.

Asexual reproduction of the new Regal *Geranium* plant by vegetative terminal cuttings in a controlled greenhouse environment in Connellsville, Pa. since March, 2001, has shown that the unique features of this new Regal *Geranium* plant are stable and reproduced true to type in successive generations.

SUMMARY OF THE INVENTION

Plants of the new Regal *Geranium* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Oglger579'. These characteristics in combination distinguish 'Oglger579' as a new and distinct cultivar of Regal *Geranium*:

1. Upright to outwardly spreading and mounded plant habit.
2. Freely branching habit.
3. Freely flowering habit.
4. Large pink and red purple bi-colored flowers.

Plants of the new Regal *Geranium* differ primarily from plants of the female parent selection in flowering time as plants of the new Regal *Geranium* flower earlier than plants of the female parent selection.

Plants of the new Regal *Geranium* differ primarily from plants of the male parent selection in the following characteristics:

1. Plants of the new Regal *Geranium* are not as vigorous as plants of the male parent selection.
2. Plants of the new Regal *Geranium* have larger flowers than plants of the male parent selection.
3. Plants of the new Regal *Geranium* and the male parent selection differ in flower color as plants of the male parent selection have lavender-colored flowers.

Plants of the new Regal *Geranium* can be compared to plants of *Pelargonium×domesticum* 'Bravo', disclosed in U.S. Plant Pat. No. 13,522. In side-by-side comparisons conducted in Encinitas, Calif., plants of the new Regal *Geranium* differed primarily from plants of 'Bravo' in the following characteristics:

1. Plants of the new Regal *Geranium* were more vigorous than plants of 'Bravo'.
2. Plants of the new Regal *Geranium* and 'Bravo' differed in flower color.

BRIEF DESCRIPTION OF THE PHOTOGRAPHS

The accompanying colored photographs illustrate the overall appearance of the new Regal *Geranium* plant, showing the colors as true as it is reasonably possible to obtain in colored reproductions of this type. Colors in the photographs may differ slightly from the color values cited in the detailed botanical description which accurately describe the colors of the new Regal *Geranium* plant.

The photograph at the bottom of the sheet comprises a side perspective view of a typical flowering plant of 'Oglger579' grown in a container.

The photograph at the top of the sheet is a close-up view of typical flowers of 'Oglger579'.

DETAILED BOTANICAL DESCRIPTION

The aforementioned photographs and following observations, measurements and values describe plants grown in 15-cm containers in Encinitas, Calif. in a polyethylene-covered greenhouse during the spring and under conditions which closely approximate Regal *Geranium* commercial production. During the production of the plants, day temperatures averaged 18° C., night temperatures averaged 10° C. and light levels averaged 4,000 foot-candles. Plants were 27 weeks old when the photographs and the description were taken. In the detailed description, color references are made to The Royal Horticultural Society Colour Chart, 2007 Edition, except where general terms of ordinary dictionary significance are used.

Botanical classification: *Pelargonium×domesticum* 'Oglger579'.

Parentage:

*Female, or seed, parent.*—Proprietary selection of *Pelargonium×domesticum* identified as code number 269, not patented.

*Male or pollen parent.*—Proprietary selection of *Pelargonium×domesticum* identified as code number 101, not patented.

Propagation:

*Type.*—By vegetative terminal cuttings.

*Time to initiate roots, summer.*—About 35 days at temperatures of 21° C.

*Time to initiate roots, winter.*—About 40 days at temperatures of 18° C.

*Time to produce a rooted young plant, summer.*—About 70 days at temperatures of 24° C.

*Time to produce a rooted young plant, winter.*—About 80 days at temperatures of 18° C.

*Root description.*—Medium in thickness, fleshy; white in color.

*Rooting habit.*—Moderate branching; moderately dense.

Plant description:

*General appearance.*—Upright to outwardly spreading and mounding plant habit.

*Growth and branching habit.*—Moderately vigorous growth habit; freely branching habit; about 16 primary lateral branches develop per plant.

*Plant height, to top of umbels.*—About 34 cm.

*Plant height, to top of foliar plane.*—About 23 cm.

*Plant diameter (spread).*—About 35 cm.

*Lateral branches.*—Length: About 16 cm. Diameter: About 7 mm. Internode length: About 2.6 cm. Texture: Pubescent. Strength: Strong. Color: Close to 144A.

Foliage description:

*Arrangement.*—Alternate; simple.

*Length.*—About 8.2 cm.

*Width.*—About 9.5 cm.

*Shape.*—Palmately lobed.

*Apex.*—Acuminate.

*Base.*—Truncate.

*Margin.*—Bi-serrate.

*Venation pattern.*—Palmate, reticulate.

*Texture, upper and lower surfaces.*—Pubescent.

*Color.*—Developing leaves, upper surface: Close to 137B. Developing leaves, lower surface: Close to 146A. Fully expanded leaves, upper surface: Close to 137A; venation, close to 137B. Fully expanded leaves, lower surface: Close to 146A; venation, close to 147C.

*Petiole.*—Length: About 3.3 cm. Diameter: About 3 mm. Texture, upper and lower surfaces: Pubescent. Color, upper and lower surfaces: Close to 146C.

Flower description:

*Flower arrangement.*—Nearly round flowers arranged in hemispherical and somewhat loose umbels arising from apical leaf axils; umbels displayed above and beyond the foliage on strong peduncles; flowers face upright or outwardly.

*Fragrance.*—Faint, sweet.

*Quantity of flowers.*—Freely flowering habit; about five to six open flowers per umbel; about 26 umbels per plant at one time.

*Flowering season.*—In California, flowering is continuous during the spring and summer.

*Flower longevity.*—Individual flowers last about seven to ten days on the plant; flowers not persistent.

*Umbel height.*—About 6.8 cm.

*Umbel diameter.*—About 9 cm to 9.5 cm.

*Flower diameter.*—About 6.8 cm by 7.2 cm.

*Flower depth (height).*—About 4.3 cm.

*Flower buds.*—Length: About 2.4 cm. Diameter: About 9 mm. Shape: Elliptical. Color: Close to 62D.

*Petals.*—Quantity per flower: Six, occasionally seven, in a single whorl. Length: About 4.3 cm to 4.6 cm. Width: About 2.3 cm to 4.5 cm. Shape: Obovate. Apex: Rounded. Base: Attenuate. Margin: Entire, sinuate. Texture, upper and lower surfaces: Smooth, glabrous; velvety. Color: When opening, upper petals, upper and lower surfaces: Towards the margins, close to 69D; towards the center, close to 58B; centers, close to N77A; base, close to NN155D. When opening, lateral and lower petals, upper and lower surfaces: Close to 69B; venation, close to 60B. Fully opened, upper petals, upper surface: Towards the margins, close to 69D; towards the center, close to N57B; centers, close to N77A; base, close to NN155D; venation, close to 59B. Fully opened, lateral and lower petals, upper surface: Close to 69B; venation, close to 60B. Fully opened, upper petals, lower surface: Towards the margins, close to NN155D; towards the center, close to 69D and 60C; centers, close to N77A; base, close to NN155D. Fully opened, lateral and lower petals, lower surface: Close to NN155D.

*Sepals.*—Quantity per flower: Six, arranged in a single whorl. Length: About 2.1 cm. Width: About 7 mm. Shape: Elliptical. Apex: Acuminate. Base: Attenuate. Margin: Entire. Texture, upper and lower surfaces: Pubescent. Color, upper surface: Close to 146C. Color, lower surface: Close to 146A to 146B.

*Peduncle* (*umbel stem*).—Length: About 4.8 cm. Diameter: About 2 mm. Strength: Strong. Texture: Pubescent. Color: Close to 146B.

*Pedicel* (*individual flower stem*).—Length: About 2.6 cm. Diameter: About 1.5 mm Strength: Strong. Texture: Pubescent. Color: Close to 144A.

*Reproductive organs.*—Androecium: Stamen quantity per flower: About ten. Anther size: About 2 mm. Anther shape: Oblong, narrow. Anther color: Close to 59C. Pollen amount: Scarce. Pollen color: Close to N34A. Gynoecium: Pistil quantity per flower: One. Pistil length: About 2.3 cm. Stigma shape: Split into six or seven parts, star-shaped. Stigma color: Close to 59A. Style length: About 1.2 cm. Style color: Close to 59D. Ovary color: Close to 138B.

*Seed/fruit.*—Seed and fruit development have not been observed.

Disease/pest resistance: Plants of the new Regal *Geranium* have not been observed to be resistant to pathogens and pests common to Regal *Geraniums*.

Temperature tolerance: Plants of the new Regal *Geranium* have been observed to tolerate temperatures ranging from about 4° C. to about 35° C.

It is claimed:

1. A new and distinct Regal *Geranium* plant named 'Oglger579' as illustrated and described.

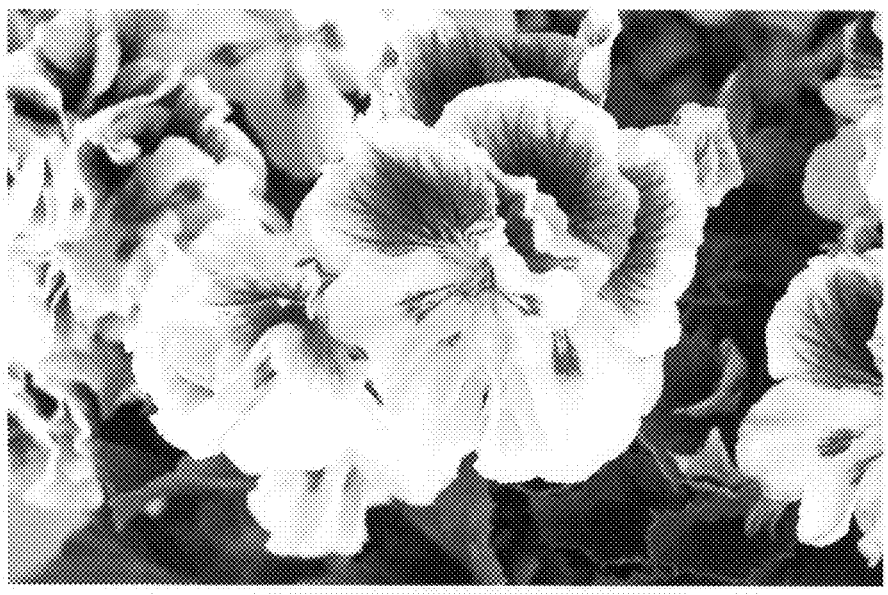
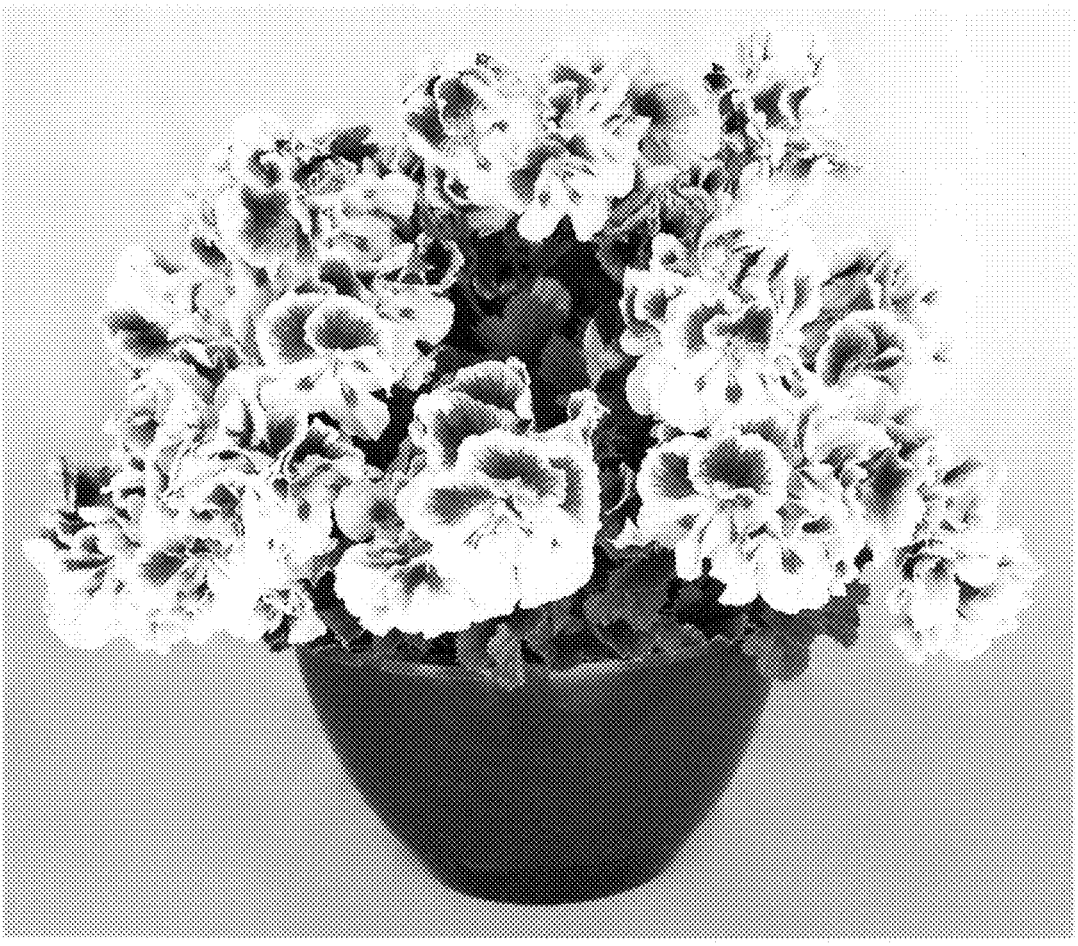

* * * * *